(12) United States Patent
Fortin et al.

(10) Patent No.: US 8,236,002 B2
(45) Date of Patent: Aug. 7, 2012

(54) DISTRACTION AND DAMPING SYSTEM WHICH CAN BE ADJUSTED AS THE VERTEBRAL COLUMN GROWS

(75) Inventors: Frédéric Fortin, Pessac (FR); Reinhard Zeller, Boulogne (FR); Alain Dimeglio, Montpellier (FR)

(73) Assignee: Siguler Guff Distressed Oppurtunities Fund III, LP, New York City, NY (US)

( * ) Notice: Subject to any disclaimer, the term of this patent is extended or adjusted under 35 U.S.C. 154(b) by 680 days.

(21) Appl. No.: 10/524,174

(22) PCT Filed: Jul. 31, 2003
(Under 37 CFR 1.47)

(86) PCT No.: PCT/FR03/02435
§ 371 (c)(1),
(2), (4) Date: Mar. 3, 2006

(87) PCT Pub. No.: WO2004/016185
PCT Pub. Date: Feb. 26, 2004

(65) Prior Publication Data
US 2007/0149909 A1 Jun. 28, 2007

(30) Foreign Application Priority Data
Aug. 13, 2002 (FR) ...................... 02 10248

(51) Int. Cl.
*A61B 17/58* (2006.01)
(52) U.S. Cl. ........................................ 606/90
(58) Field of Classification Search ............ 606/57, 606/105, 246, 250–251, 257; 602/32; 623/17.11–17.13
See application file for complete search history.

(56) References Cited

U.S. PATENT DOCUMENTS
3,900,025 A 8/1975 Barnes, Jr.
(Continued)

FOREIGN PATENT DOCUMENTS
CA 2 451 977 A1 11/1993
(Continued)

OTHER PUBLICATIONS
Office Action dated Apr. 18, 2008, in U.S. Appl. No. 10/760,075, filed Jan. 18, 2004.
(Continued)

*Primary Examiner* — Eduardo C Robert
*Assistant Examiner* — Tara Carter
(74) *Attorney, Agent, or Firm* — Tram Anh Nguyen

(57) ABSTRACT

The invention related to a distraction and damping system which combines two devices, namely a first distractor device and one or more other damping devices. The aforementioned distractor device is for children's bones and can support and lengthen said bones by means of rods which are mounted to an adjustment means. Moreover, said distraction and damping system is hooked to the bones at the ends of the rods which are connected to hooks. The above-mentioned damping devices consist of flexible and rigid means. The inventive system, which results from the combination of said two devices, comprises the implantation of novel means such as serrated rods, one of the ends of which takes the form of a piston head. Said system his intended to be used in order to straighten and support a child's torso and his/her vertebral column, by acting on the central means by tightening the screws; dampen dynamic loads; be adjustable according to growth, the system being re-adjusted as often as necessary; and prevent significant stresses from being created in the bones, in particular, at the hooks, without impeding growth.

10 Claims, 9 Drawing Sheets

U.S. PATENT DOCUMENTS

| | | | |
|---|---|---|---|
| 4,386,603 A | | 6/1983 | Mayfield |
| 4,445,674 A | | 5/1984 | Clayton, Jr. |
| 4,611,582 A | | 9/1986 | Duff |
| 4,658,809 A | | 4/1987 | Ulrich et al. |
| 4,747,394 A | | 5/1988 | Watanabe |
| 4,931,055 A | | 6/1990 | Bumpus et al. |
| 5,129,903 A | | 7/1992 | Luhr et al. |
| 5,130,356 A | | 7/1992 | Feuerherd et al. |
| 5,261,908 A | * | 11/1993 | Campbell, Jr. ............... 606/279 |
| 5,375,823 A | * | 12/1994 | Navas ..................... 623/17.15 |
| 5,395,370 A | | 3/1995 | Muller et al. |
| 5,503,413 A | | 4/1996 | Belogour |
| 5,672,175 A | | 9/1997 | Martin |
| 5,700,263 A | | 12/1997 | Schendel |
| 5,885,283 A | | 3/1999 | Gittleman |
| 6,241,730 B1 | * | 6/2001 | Alby ........................ 606/256 |
| 6,382,602 B1 | | 5/2002 | Morrow |
| 6,402,750 B1 | * | 6/2002 | Atkinson et al. ............ 606/279 |
| 7,029,472 B1 | | 4/2006 | Fortin |
| 2002/0074881 A1 | * | 6/2002 | Imlach ...................... 310/90.5 |
| 2002/0151978 A1 | * | 10/2002 | Zacouto et al. ............ 623/17.12 |
| 2004/0097938 A1 | | 5/2004 | Alleyne |
| 2004/0153067 A1 | | 8/2004 | Smith et al. |
| 2005/0056979 A1 | | 3/2005 | Studer et al. |
| 2005/0165396 A1 | | 7/2005 | Fortin et al. |
| 2005/0182401 A1 | * | 8/2005 | Timm et al. .................... 606/61 |
| 2005/0261685 A1 | | 11/2005 | Fortin et al. |

FOREIGN PATENT DOCUMENTS

| | | |
|---|---|---|
| DE | 24 37 752 A1 | 2/1976 |
| DE | 19500202 | 7/1996 |
| EP | 0576379 | 12/1993 |
| FR | 2692952 A1 | 12/1993 |
| FR | 2717370 | 9/1995 |
| FR | 2730156 | 8/1996 |
| FR | 2774581 | 8/1999 |
| FR | 2 794 357 A | 12/2000 |
| FR | 2 814 936 A | 4/2002 |
| WO | WO 90/12553 A1 | 11/1990 |
| WO | WO 98/22033 | 5/1998 |
| WO | WO 0072768 A1 * | 12/2000 |

OTHER PUBLICATIONS

Office Action dated Jul. 17, 2006, in U.S. Appl. No. 10/760,075, filed Jan. 18, 2004.
Office Action dated Oct. 7, 2008, in U.S. Appl. No. 10/505,469, filed Aug. 20, 2004.
Office Action dated Jul. 7, 2006, in U.S. Appl. No. 10/505,469, filed Aug. 20, 2004.
U.S. Appl. No. 12/083,184, filed Apr. 4, 2008, by Fortin et al.
French Search Report and Written Opinion for Application No. FR 0510207, dated Jul. 25, 2006.
French Search Report for Application No. FR 0109628, dated Apr. 9, 2002.
French Search Report for Application No. FR 0210248, dated Apr. 11, 2003.
French Search Report for Application No. FR 9907034, dated Feb. 15, 2000.
International Search Report for International Application No. PCT/FR00/01427, mailed Sep. 6, 2000.
International Search Report for International Application No. PCT/FR02/02547, mailed Nov. 25, 2002.
International Search Report for International Application No. PCT/FR03/02435, mailed Feb. 27, 2004.
International Search Report for International Application No. PCT/FR2006/002225, mailed Apr. 4, 2007.
Office Action in U.S. Appl. No. 10/505,469, mailed May 8, 2009.
Office Action in U.S. Appl. No. 10/760,075, mailed May 26, 2009.
Written Opinion for International Application No. PCT/FR2006/002225, mailed Apr. 5, 2007 (French).
Office Action issued in European Patent Application No. 03778377.6, dated Jul. 30, 2009 (French), with English Translation.
Office Action issued in U.S. Appl. No. 10/505,469, dated Dec. 8, 2009.
Notice of Allowance issued in U.S. Appl. No. 10/760,075, dated Jan. 25, 2010.

* cited by examiner

PRIOR ART

US 8,236,002 B2

DISTRACTION AND DAMPING SYSTEM WHICH CAN BE ADJUSTED AS THE VERTEBRAL COLUMN GROWS

FIELD OF THE INVENTION

The invention relates to an adjustable distraction and support device implanted on the trunk of a child incorporating a combination of several devices used to straighten, support and cushion the mechanical stresses and which can be readjusted according to the growth of the child, these functions not being attainable through the use of each device separately.

BACKGROUND OF THE INVENTION

Patent Fr 9907034, directed toward a chest wall distractor, describes and claims a mechanical device that can monitor the growth of the bones in incorrect formation while correcting the deformities of the trunk without prohibiting or obstructing the patient's growth, but it is limited in its application to a deformity at the level of the thorax; it cannot be applied to a deformity involving the lumbar spine of the child since his or her growth could be impaired by placing the device directly on the vertebrae.

Patent Fr 109628000, entitled *Flexible vertebral linking device consisting of elements that allow the overcoming of a spinal deformity*, is largely a cushioning device comprised of rigid components holding visco-elastic means that can cushion the mechanical stresses in the preferred directions.

This device was designed to offset the stresses sustained by the vertebrae of the human body in a multi-axial fashion; it was not intended to be lengthened during displacements by stretching as is the case of the device described in the previous patent.

SUMMARY OF THE INVENTION

The device of the present invention allows the steadying of the thorax while allowing the lungs to develop, the straightening of the spine completely during growth without blocking the vertebrae, the cushioning of the external mechanical stresses, the use of an adjustment system that can be accessed easily and does not require a extensive or invasive surgical procedure.

The anchoring devices of the first device resulting from the first invention (patent Fr 9907034) are formed through the use of anchoring brackets surrounding the bones; this first device lending itself perfectly to the fasteners of the thorax would however exert considerable stress on the fasteners used to secure the lumbar vertebrae, which would lead to a risk of rupture in particular for the anchoring screw, which is, of course, unacceptable.

The present invention solves this problem because of its capacity to resolve the difficulties stemming from large deformities by including the lumbar spine.

In the search report for the French patent application (filing 0210248), three prior documents are compared. In U.S. Pat. No. 6,402,750 B1, the only comparable device is the piston, which in this invention can only move axially, it being unable to follow a curvilinear path in phase with the shape of the spine. For an adjustment, this device has to be completely dismantled, which requires a major surgical procedure. In no way is this the case for our invention, which requires only a minor surgical procedure under local anesthesia in order to adjust a central means, the access to which requires only a small incision made under the skin.

Patents FR 2794357 and FR 2814936, dealing firstly with two devices designed independently and that could not be combined without being modified, demonstrates to a person skilled in the art the non-obviousness of this combination, and therefore constitutes a proof of inventiveness. The result that was obtained was not guaranteed in any way. It was made possible as a result of the creation and implantation of new means such as toothed rods, which can be bent as needed and one of the ends of which is shaped like a piston. The unexpected result was the smooth operation of the device, showing that the implementation of this invention combining two prior devices was carried out following numerous tests performed with various radii of rod curvature, characteristics that are distinguished from the prior art.

BRIEF DESCRIPTION OF THE DRAWINGS

The following drawings may aid a better understanding of the invention.

DETAILED DESCRIPTION OF THE INVENTION

Device 2, combining devices 3 and 1, consists of a device 3 called the distraction device intended for children's bones and of a device 1 called device for cushioning the mechanical stresses.

Figure 1:
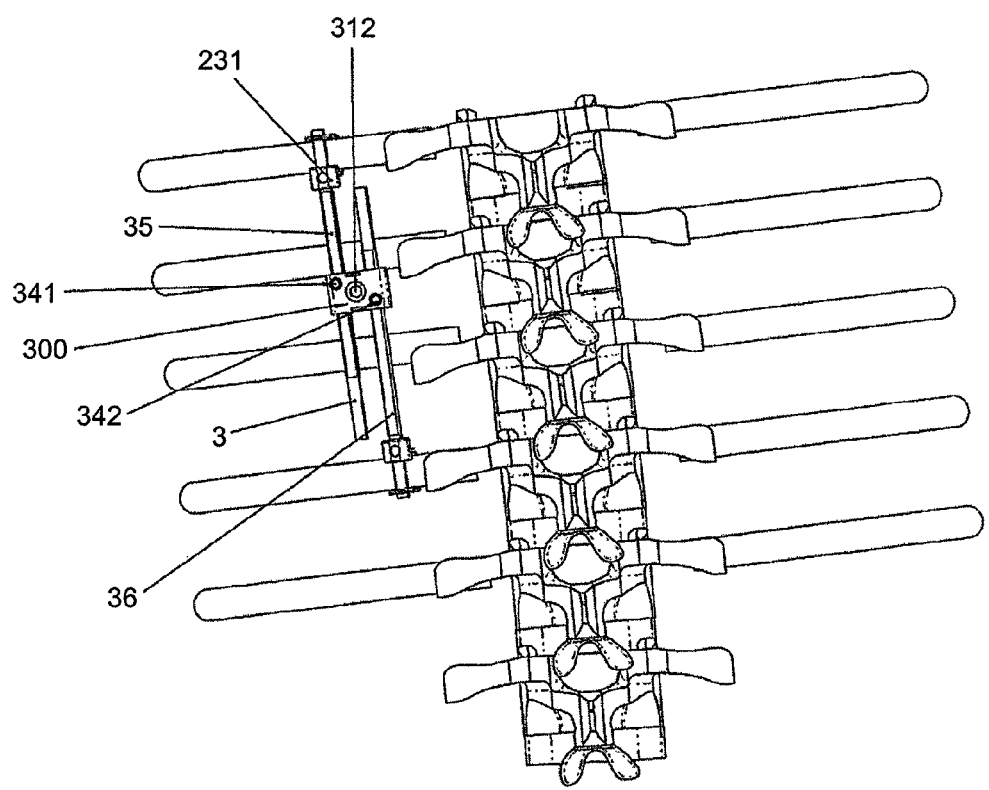
FIG. 1 is a distraction device intended for the bones of children (prior art).
Figure 2A:
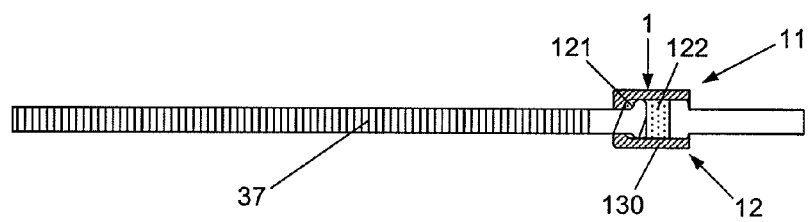
FIGS. 2A and 2B are a flexible and cushioning connecting device consisting of two rods, one of which includes teeth to be used as a pinion (rectilinear or curved rods).
Figure 2B:
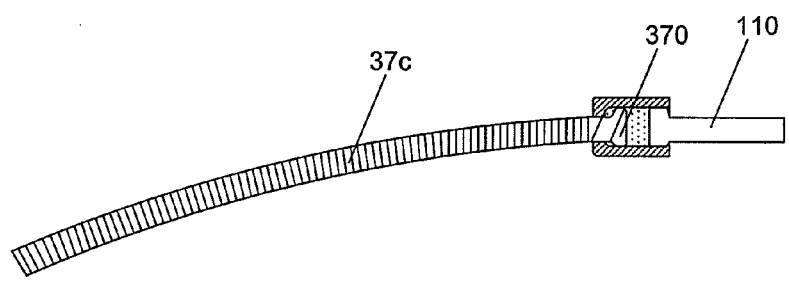
Figure 3:
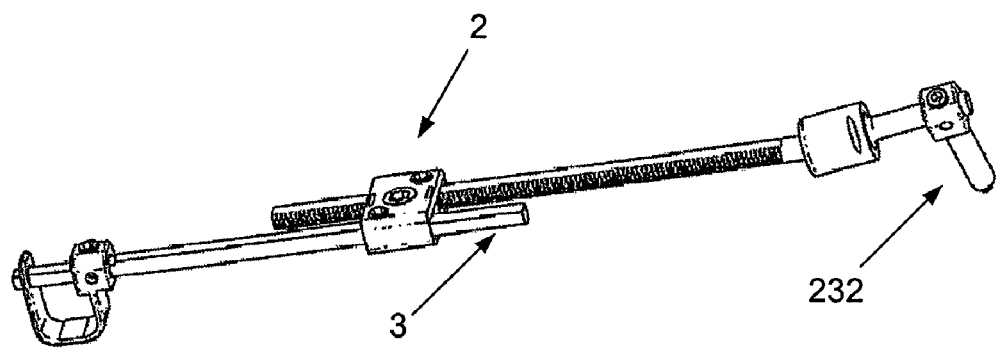
FIG. 3 is the first example of a device which combines the distraction device intended for the child's bones with the flexible and cushioning connecting device.
Figure 4:
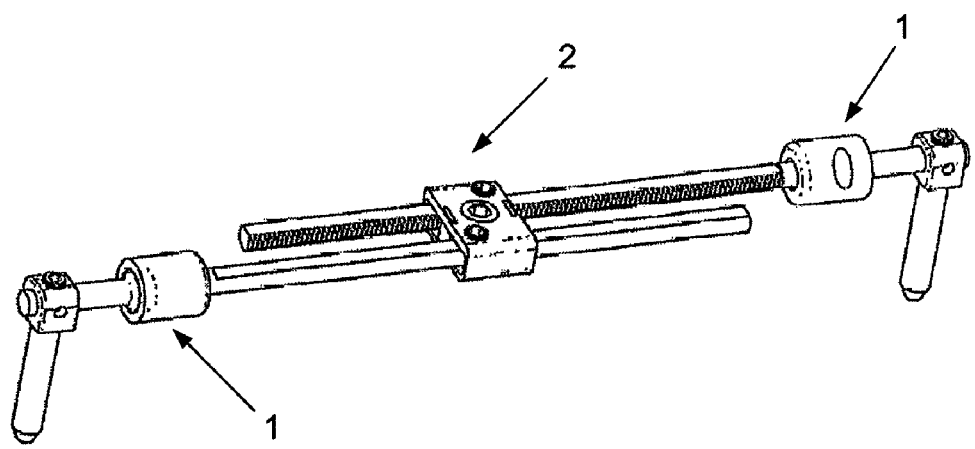
FIG. 4 is the second example of the device which combines the distraction device with two flexible and cushioning connecting devices.
Figure 5:
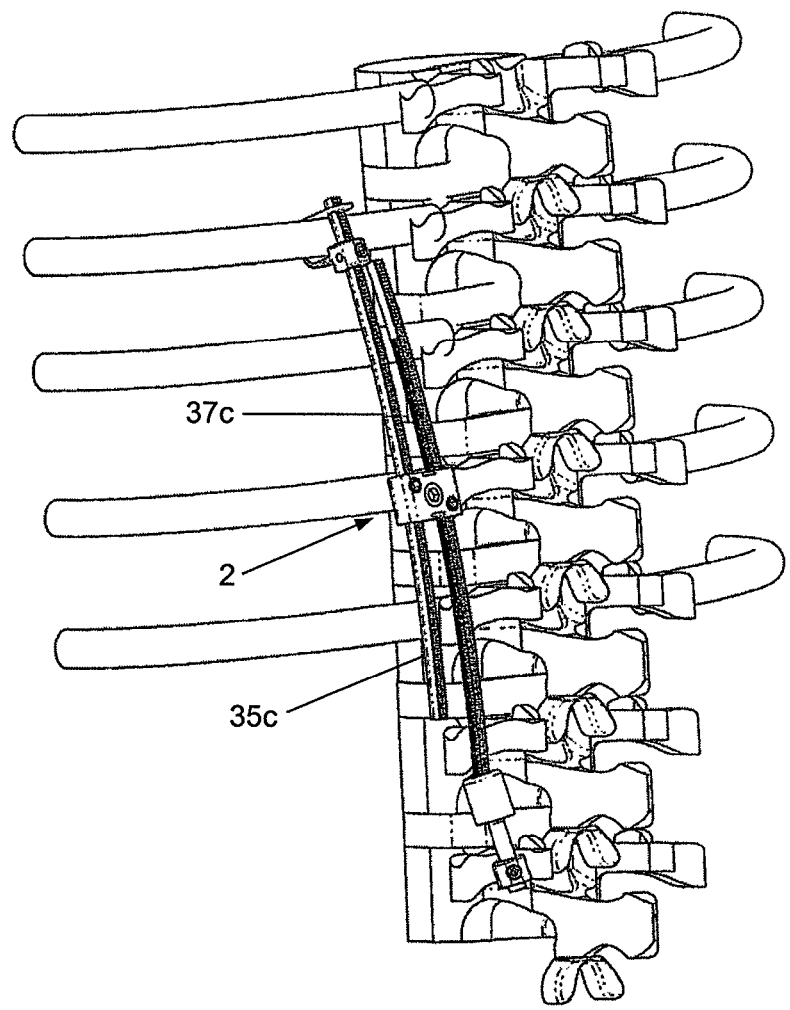
FIG. 5 is a device which combines both devices placed on a rib and on a vertebra and includes two curvilinear distraction rods.

The device 2 (FIG. 3) thus formed allows simultaneously the straightening of the spine and steadying of the trunk of a child, the monitoring growth and the lengthening of the anchoring distances by minor surgical procedures, the alleviation of the mechanical loads exerted via anchoring means, the cushioning of the mechanical stresses.

This invention can be better understood if we recall briefly the means used in devices 3 and 1.

Device 3 allows the monitoring of the course of the deformity of a child's trunk; it can be implanted in the human body easily, due to its small size.

Two toothed rods 35 and 36 mounted on a central means 300 equipped with a hole 312 through which a tool can be inserted to adjust the distance from the anchoring devices 231 to the bones; the device is locked in place in a position determined by tightening the two screws 341 and 342 located on the central means 300.

As shown in the prior art, rods 35 and 36 were rectilinear and could have curved ends to ease placement of the anchoring devices, while the present device 2 may include arched or curved rods 35c and 37c, along their entire length. In this case, test results have shown a normal operation of the device. The advantage gained from this improvement is that damage to the surrounding tissues can be avoided by lengthen the anchoring distances by carefully following a curvature chosen at the beginning by the operator. Moreover, this curvature may be adjusted due to the malleability of the material constituting the rods, which, after testing, can be deformed by the operator.

The flexible intervertebral linking device 1 is itself comprised of two sets of means a first set of means 11 comprised of rigid means 110, 130, and 37 made of biocompatible material assuring a good mechanical bond of the device by transmitting the stresses completely without being deformed, and second set of means 12 made of flexible and cushioning means 121 and 122 made of biocompatible visco-elastic material, accepting repeated elastic deformations, the combination of both sets of means allowing the withstanding and cushioning of the mechanical stresses to which it will be subjected, in order to overcome any dysfunction in the spinal linkage.

Each of devices 3 and 1 have means which are compatible by their design and main functions to which are added new means allowing them to be combined.

As we have already mentioned, device 3 can receive rectilinear or curvilinear rods that are curved at various radii. A device 2 can be positioned consisting of a device 3 having a rectilinear rod 37 on one side, and a curved or arched rod 35c on the other side.

Figure 6:
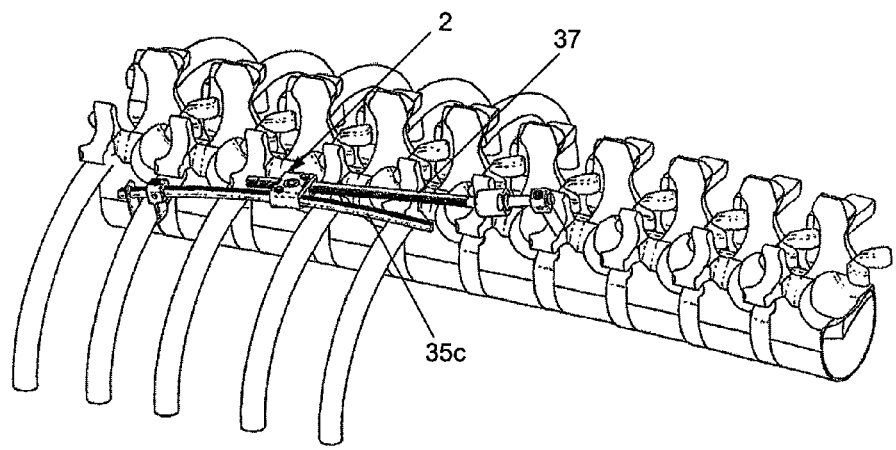
FIG. 6 is another example of the device implemented on a rib and a vertebra and including rectilinear and curvilinear distraction rods.
Figure 7:
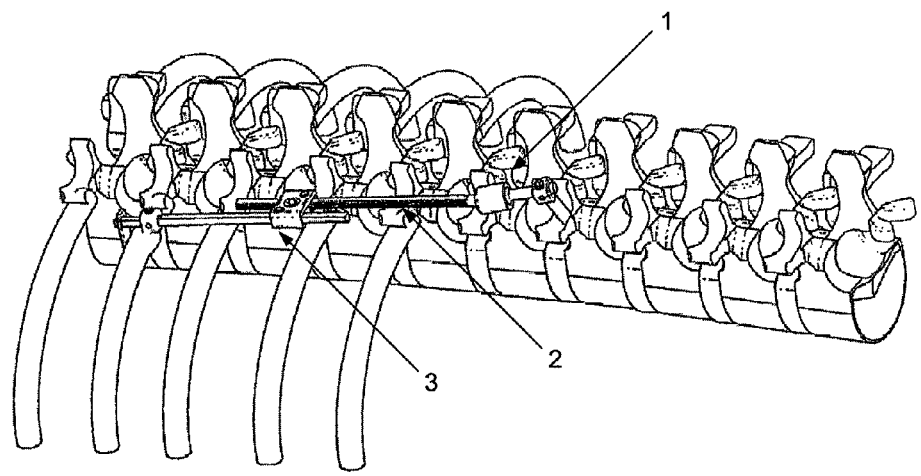
FIG. 7 is a device working with rectilinear rods.
Figure 8:
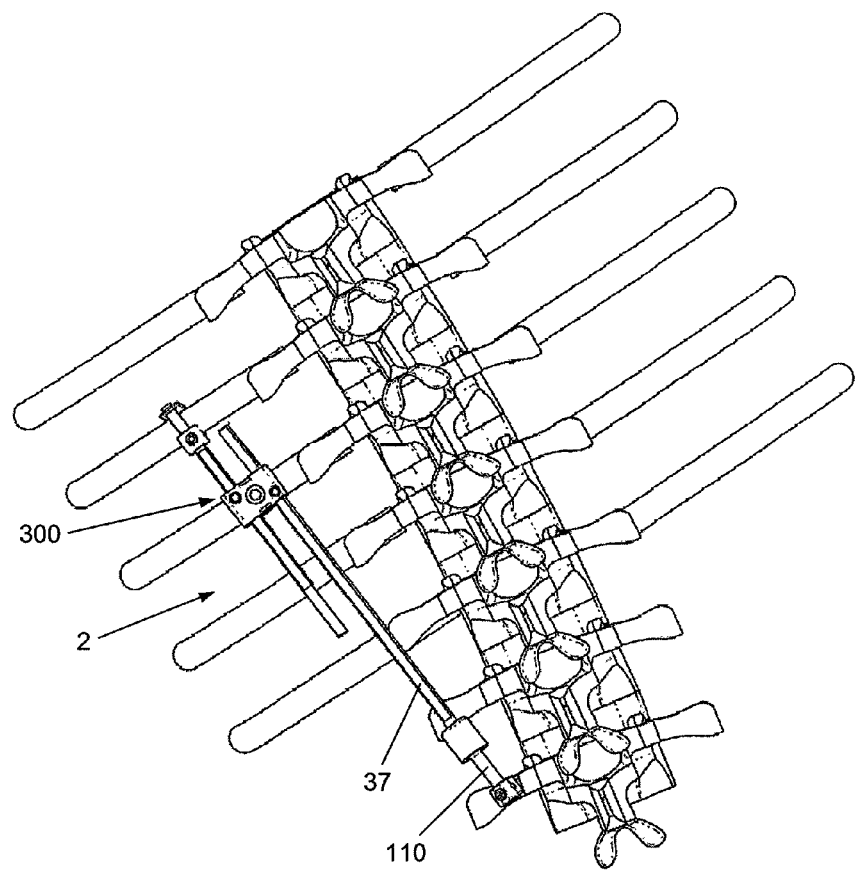
FIG. 8 is the placement of the device on a deformed trunk.

In this latter case, 35c is curved to avoid causing injury and to allow lengthening near the anatomic curve (FIG. 6). Device 2 resulting from the combination of devices 3 and 1 allows the straightening of the trunk by adjustment of the central means 300 and its means 312, 341 and 342 through a highly targeted, surgical procedure only slightly invasive and performed under local anesthesia.

The distraction device 2 includes at least one rectilinear or curvilinear toothed rod 37 or 37c, one end of which includes a cylindrical plate 370 perfectly integrated into the visco-elastic means 121 and 122 and rigid means 130 of device 1, allowing the distraction device 2 to be cushioned and to cling to a vertebra even though beforehand it is out of alignment with the distraction device 3.

Thus, the trunk is straightened with the central means 300, which is locked into place with screws 341 and 342 using a small Allen wrench inserted in screw 312 through a small opening requiring only minor surgery. Device 2 can then perform its function of supporting the straightened trunk.

Figure 9:
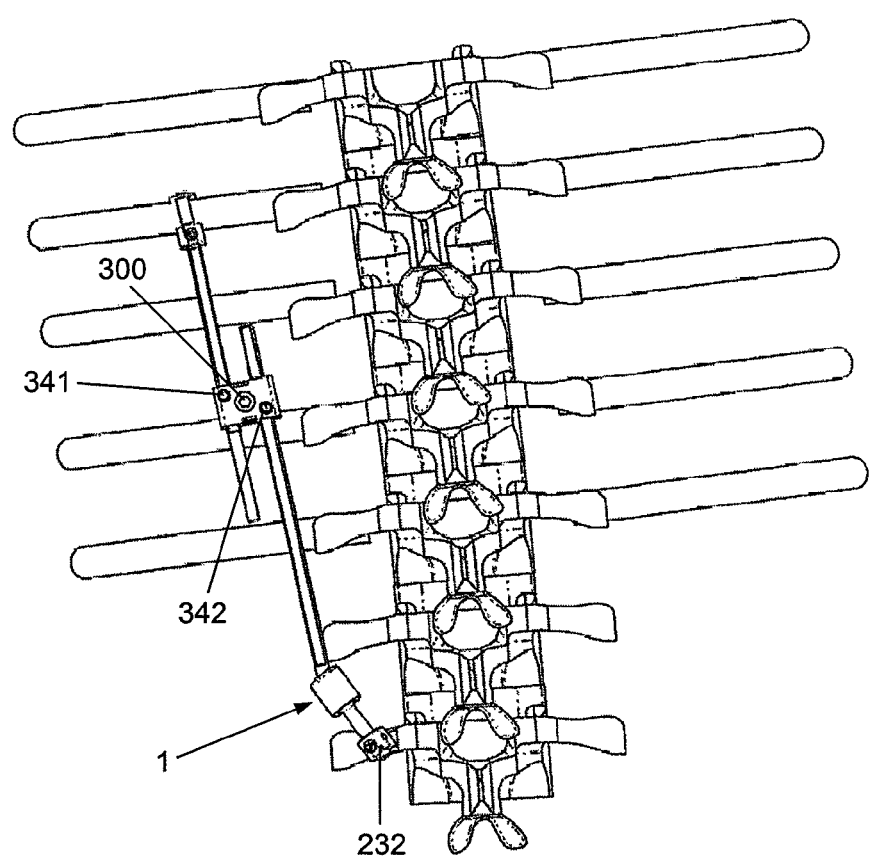
FIG. 9 is a view of the device following the straightening of the initially deformed trunk with the cushioning device positioning itself crosswise under the influence of the straightening forces.
Figure 10:
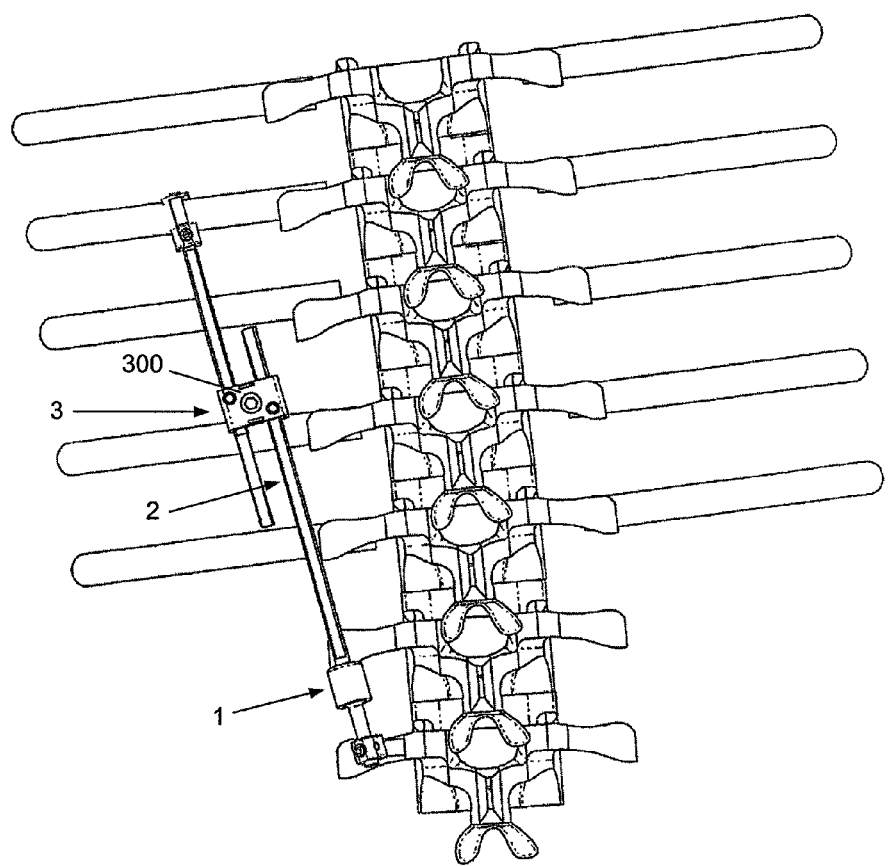
FIG. 10 is a view of the compound device, the cushioning device being less strained due to the child's growth.

After growth, device 2 is examined and in particular the alignment of rod 37 with rod 110; the operator may then modify means 300 in an effort to straighten the trunk again. Following the straightening efforts, the cushioning device 1 that is part of device 2 is positioned slightly crosswise (FIG. 9), thus serving as a growth and force indicator to determine the straightening needs on a case by case basis. In the case where a device 2 is positioned on the trunk of a child at the beginning of growth, the cushioning device 1 can be placed between a screw anchoring to a vertebra and rod 37 designed to ensure the linkage with device 3 (FIG. 9, Means 232). This device 2 authorizes and allows the monitoring of the child's growth while preventing significant stresses being exerted on the anchoring screw 232 (FIG. 10). By absorbing the shocks and the dynamic stresses in said bone screws 232, the visco-elastic means 121 and 122 will avoid ruptures. The shift to the "alignment" position of rods 110 with 37 or 37c is a reliable indicator.

If both rods are aligned, it is again necessary to restore the tension to the device since the stresses applied to device 1 have decreased and the two rods are again on the same axis as a result of the elasticity of device 1 and of the growth of the child.

In addition to the limitations on the stresses exerted on the screws following the straightening of the trunk, device 1 cushions the exterior mechanical stresses and as a result its flexibility will not restrict vertebral mobility.

The various straightening and steadying maneuvers on a child's trunk can easily be repeated; consequently, device 2 may be adjusted as many times as is necessary through a highly localized procedure performed on means 300.

Figure 11:
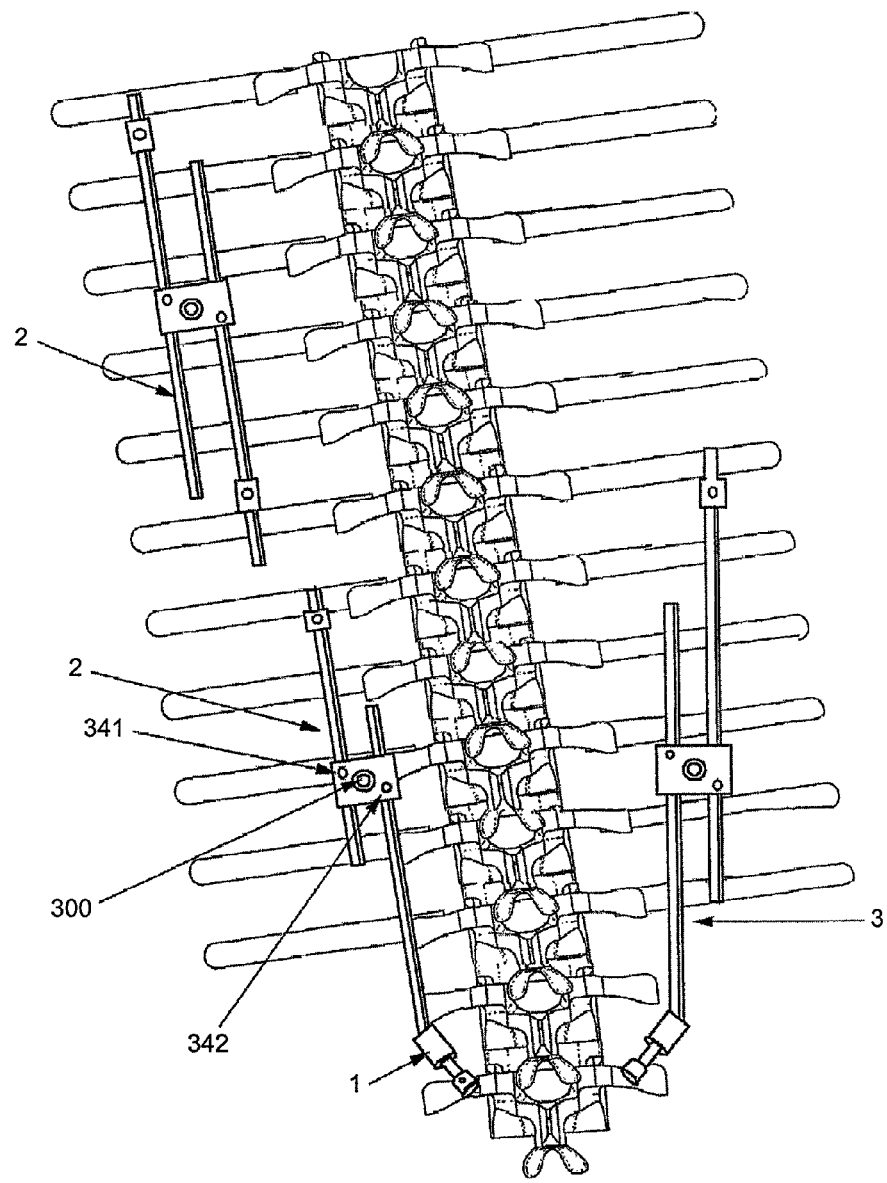
FIG. 11 shows the placement of several devices on a trunk in order to completely control and straighten the trunk.

In addition, the multiple combinations of means 1 and 3 allow placing several devices 2 on the spine (FIG. 11) to monitor the growth and straighten the trunk.

The invention claimed is:

1. A distraction and damping device for attachment to a child's thorax and spine, comprising:
  a first rod member having a first end;
  a second rod member have a second end;
  a mechanical coupler connecting the first rod member to the second rod member and allowing adjustment of a distance between the first end of the first rod member and the second end of the second rod member to straighten the spine of a patient; and
  a first damping member, having a first end coupled to the first end of the first rod member and a second end configured to be coupled to a first bone structure, the first damping member comprising a combination of a rigid element and a biocompatible viscoelastic element configured to allow cushioning of mechanical stresses;
  wherein the first rod member can translate linearly within the first damping member to adjust the alignment of the first rod member along a longitudinal axis of the first damping member, and wherein at least one of the first rod member and the second rod member is curved along its entire length; further wherein the device allows for simultaneous straightening of the spine and steadying of the thorax of the child during growth.

2. The device of claim 1 wherein the first damping member comprises:
  a rigid cylinder;
  a first elastic member disposed within the rigid cylinder; and
  a second elastic member disposed within the rigid cylinder, wherein the first end of the first rod member includes an enlarged distal portion disposed between the first elastic member and second elastic member.

3. The device of claim 1, wherein at least one of the first rod member and the second rod member is serrated.

4. The device of claim 1, wherein at least one of the first rod member and the second rod member are constructed from a malleable material and the curvature of the at least one of the first rod member and the second rod member can be adjusted.

5. The device of claim 1, wherein the first rod member and the second rod member are both curved.

6. The device of claim 1, wherein the second end of the first damping member is configured to be coupled to a vertebra.

7. The device of claim 1, wherein the second end includes a hook member configured to engage a rib.

8. The device of claim 1, further comprising:
a second damping member, having a first end coupled to the second end of the second rod member and a second end configured to be coupled to a second bone structure.

9. The device of claim 8 wherein the second damping member comprises:
a rigid cylinder;
a first elastic member disposed within the rigid cylinder; and
a second elastic member disposed within the rigid cylinder, wherein the second end of the second rod member includes an enlarged distal portion disposed between the first elastic member and second elastic member.

10. The device of claim 8, wherein the second end of the second damping member is configured to engage a rib.

* * * * *